United States Patent
Brenner et al.

(10) Patent No.: US 6,537,500 B1
(45) Date of Patent: Mar. 25, 2003

(54) PROCESS FOR THE DETECTION OF A PRODUCT IN THE DISCHARGE OF A CATALYTIC MATERIAL OF A PLURALITY OF CATALYTIC MATERIALS

(75) Inventors: Armin Brenner, Spiesheim (DE); Armin Lange de Oliveira, Muhlheim (DE); Ferdi Schuth, Muhlheim (DE); Stephan Schunk, Frankfurt/Nied (DE); Wolfram Stichert, Heidelberg-Kirchheim (DE); Klaus Unger, Seeheim-Jugenheim (DE)

(73) Assignee: hte Aktiengesellschaft, Heidelberg (DE)

( * ) Notice: Subject to any disclaimer, the term of this patent is extended or adjusted under 35 U.S.C. 154(b) by 0 days.

(21) Appl. No.: 09/350,459

(22) Filed: Jul. 9, 1999

(30) Foreign Application Priority Data

Sep. 7, 1998 (DE) .......................... 198 30 607

(51) Int. Cl.[7] .............................................. G01N 30/96
(52) U.S. Cl. ............................ 422/88; 422/86; 422/83; 436/37; 436/181; 436/178; 436/167
(58) Field of Search ..................... 422/86, 88, 83; 436/37, 181, 178, 167

(56) References Cited

U.S. PATENT DOCUMENTS

| | | | |
|---|---|---|---|
| 5,284,054 A | 2/1994 | Loebach ..................... | 73/23.3 |
| 5,411,709 A | 5/1995 | Furukui et al. ............... | 422/91 |
| 5,911,953 A | 6/1999 | Ogata et al. .................. | 422/91 |

FOREIGN PATENT DOCUMENTS

| | | | |
|---|---|---|---|
| AU | 731245 | 3/1998 | ......... G01N/031/10 |
| DE | 197 24 655 A | of 1997 | .......... G01N/21/35 |
| DE | 196 32 779 A1 | 2/1998 | .......... G01N/35/00 |
| WO | WO 91 01001 | of 1991 | .......... G01N/31/22 |
| WO | WO 97/32208 | 9/1997 | .......... G01N/31/10 |

OTHER PUBLICATIONS

Infrared Thermographic Screening of Combinatorial Libraries of Heterogeneous Catalysts, Ind. Eng. Chem. Res. 1996, pp. 4801–4803, F.C. Moates, M. Somani, J. Annamalai, J.T. Richardson, D. Luss, and R.C. Willson.

Determination of sub–ppbv levels for formalydehyde in ambient air using Girard's reagent T–coated glass fiber filters and adsorption voltametry, Analytica Chimica Acta 349 (1997) pp. 349–357, Wing Hong Chan, Tian Xao Xie.

Development of a monitoring tape for nitrogen dioxide in air, Analytica Chemica Acta 321 (1996), pp. 41–45, N. Nakano.

*Primary Examiner*—Jill Warden
*Assistant Examiner*—Sam P. Siefke
(74) *Attorney, Agent, or Firm*—Heslin Rothenberg Farley & Mesiti P.C.

(57) ABSTRACT

Process for the detection of a product in the discharge of a catalytic material of a plurality of catalytic materials which are exposed to a reaction gas, whereby an adsorbent selective for the product to be determined is disposed in the discharge of each catalytic material, which changes at least one of its properties through the contact with the product to be determined and the change in the property of the adsorbent is then ascertained.

The process serves in particular to determine the selectivity and activity of catalytic materials.

20 Claims, 1 Drawing Sheet

PROCESS FOR THE DETECTION OF A PRODUCT IN THE DISCHARGE OF A CATALYTIC MATERIAL OF A PLURALITY OF CATALYTIC MATERIALS

BACKGROUND OF THE INVENTION

The invention relates to a process for the detection of a product in the discharge of a catalytic material of a plurality of catalytic materials which are exposed to a reaction gas.

The development of new, especially more effective catalysts is required to improve the yield of many standard processes. In order to produce and characterise catalysts, the potentially active carrier and catalyst components are combined in a supposedly suitable manner and the multi-component mixtures thus created are tested with a suitable test reaction under defined conditions usually determined by technical limitations. Whilst the synthesis of such materials can often still be managed with reasonable time consumption, the testing of the catalysts on the contrary represents a very time- and labour-consuming step. The material to be tested is generally poured into a laboratory test reactor specially designed for the purpose and tested under prescribed parameters for its suitability for the given conversion of an educt mixture.

Gas chromatographic or spectroscopic methods are chiefly used to characterise catalysts. These methods, however, have only a limited suitability for the simultaneous testing of many catalysts. Whereas gas chromatography has the drawback that it requires a certain period of time, the spectroscopic methods have the drawback that, in the case of complicated reactions, they give insufficient information about the selectivities of the catalysts. Both methods also have the drawback that they only function sequentially and involve an elaborate and costly analysis.

Nonetheless, progress has been made with the applicability of both these methods. Through the computer-controlled combination of several columns, for example, an improvement has been achieved in the analysis quality and the analysis speed in gas chromatography (Stockinger, J. H., Callen, R. B., Kaufman, W. E., J. Chromatogr. Sci. 16, 1978, 418).

The use of spectroscopic methods for characterising samples is described in connection with a process for investigating chemical reactions in reactors connected in parallel (Windhab, N., Miculka, C., Hoppe, H.-U., DE 196 32 779).

A method of testing catalyst pellets with the aid of infrared thermography has also been published (Moates, F. C., Somani, M., Annamalai, J., Richardson, J. T., Luss, D., Willson, R. C., Ind. Eng. Chem. Res. 35, 1996, 4801). This method, however, is limited to reactions with great heat of reaction. An additional drawback with this method lies in the fact that, with partial oxidations for example, the hottest catalyst is not the one with the greatest selectivity for the desired product.

WO 97/32208 describes a catalyst testing process, in which a plurality of differently composed catalysts in the form of pellets or suchlike are arranged in a multi-cell holder and brought into contact with an inflow of a mixture. The measurement takes place spectroscopically, thermographically or with the aid of other commonly used measuring methods, whereby the measurement is always carried out directly on the catalysts.

DE 196 33 779 A1 describes a process for investigating chemical reactions in miniature reactors connected in parallel. The supplied educt is led past a catalyst in each case, as a result of which a reaction mixture arises which in turn is passed in each case into a cell drill-hole and separated out via the latter. For the measurement, an infrared beam extends in each case through one of the cell drill-holes which are arranged in the manner of an nxn matrix.

In the light of the prior art, the problem of the present invention is to make available an economically practicable process for the detection of a product in the discharge of a catalytic material of a plurality of catalytic materials which are exposed to a reaction gas, in order to establish the selectivity and activity of the catalytic materials.

Furthermore, the problem of the invention is to provide a method for the testing of catalytic materials that is as cost-effective, simple and efficient as possible.

The process should further be able to be carried out without taking a great deal of time and effort.

BRIEF SUMMARY OF THE INVENTION

These problems, as well as other problems not explicitly stated but which can readily be derived or inferred from the context discussed herein, are solved by the measures described in claim 1. Expedient modifications of the process according to the invention are protected in the sub-claims related back to claim 1.

By disposing an adsorbent selective for the product to be determined in the discharge of each catalytic material, which changes at least one of its properties through the contact with the product to be determined, and then by ascertaining the change in the property of the adsorbent, it is possible to ascertain the selectivity and activity of the catalytic materials.

On the one hand, the process is cost-effective and efficient, and on the other hand the process can be carried out without taking a great deal of time and effort.

The arrangement for the analysis can be spatially separate from the catalytic material. The analysis of the products can thus be carried out by means of methods that cannot be used under the reaction conditions of the catalytic conversion, because for example the adsorbent is not stable at the temperatures at which the catalysed reaction must take place. If the adsorbent is not destroyed by the selected reaction conditions, it can however also be spatially very close to the catalytic material.

By means of a suitable arrangement of various adsorbents, different products of the catalytic reaction can be determined simultaneously. It is thus possible in a very elegant manner to determine, apart from the activity of a catalytic material in respect of a desired product, also the concentration of undesired by-products, so that the selectivity of the catalytic material can also be determined.

Preferred forms of embodiment of the process according to the invention are characterised by the fact that the adsorbent is a solid or a liquid applied to a solid carrier.

Preferably, an optical property, especially in the infrared, visible or ultraviolet region, is changed by the contact with the product to be determined.

It is particularly preferable for a colour change to occur through the contact of the adsorbent with the product of the catalytic conversion to be determined, so that for example a colour formation or a decolourisation can be ascertained.

It is further preferred that the property of the adsorbent changing through the contact with the product to be determined is a fluorescence.

A further property that can be changed by the contact with the product to be determined is the weight of the adsorbent.

A further preferred modification of the process according to the invention employs the temperature of the adsorbent to determine a product of the catalytic reaction.

A further property of the adsorbent that can be changed by the contact with the product to be determined is the refractive index of a liquid applied to a solid carrier.

Furthermore, the pH of the adsorbent is a property that can be changed by the contact with the product to be determined, especially when the adsorbent is a liquid applied to a solid carrier.

It is particularly preferable for a change in the conductivity of the adsorbent to occur through the contact with the product to be determined.

The product to be determined can also be dissolved out of the adsorbent with the aid of a solvent, after which a property, such as for example the refractive index, the pH value and the conductivity, of the solution thus obtained is determined.

Preferred forms of embodiment of the process according to the invention are characterised in that the product to be determined is maleic anhydride and the adsorbent is an N,N-dimethylindoanyline applied in ethanol solution onto a filter paper, whereby the colour of the adsorbent changes from blue to colourless upon contact with the maleic anhydride.

In a preferred form of embodiment of an adsorbent described above, reactive groups capable of reacting selectively with a desired product in the discharge of a parallel reactor are applied to a solid carrier.

In a further preferred form of embodiment, reactive molecules capable of reacting selectively with a desired product are dissolved in a solvent, after which the latter is applied to a solid carrier.

Detection of a product should be understood within the scope of the present invention to mean any identification of a chemical element, a chemical compound or a functional group which are formed in a catalytic reaction.

It can relate here, for example, to a compound whose formation is intended to be optimised by the catalytic conversion.

It is however also conceivable for a compound to be determined that necessarily arises with the formation of the desired product. Amongst others, this includes for example hydrogen which is liberated in a dehydrogenation.

By means of the process according to the invention, however, substances can also be detected whose formation is to be avoided, i.e. by-products of a catalytic conversion.

A catalytic material is a substance which lowers the activation energy for the course of a certain reaction and thus increases the reaction rate, without appearing in the end product of the reaction. Substance is understood here to mean for example elements and compounds as well as homogeneous and heterogeneous mixtures thereof. Binary or ternary mixtures of elements and/or compounds in particular often display an unexpectedly high catalytic effect which can only be ascertained empirically.

The process according to the invention makes it possible to investigate simultaneously under identical reaction conditions many catalytic materials which differ in their composition. The essential feature of the invention here is that the discharge of a catalytic material can be assigned to a change in the property of the adsorbent. It may be necessary here for the discharges of the respective catalytic materials to be kept separate from one another. The plurality of catalytic materials, i.e. at least two, can for example be introduced into parallel reactors.

Discharge is understood to mean the gas mixture after the contact with a catalytic material, which can contain at least one reaction product. The reaction gas is a gas that contains the reactant or reactants. It can in addition contain inert gases, such as for example nitrogen or noble gases (in particular helium, neon, argon or mixtures of these gases), in order for example to improve the conducting of the reaction.

Reactant is understood here to mean the starting substance or starting substances of a catalytic conversion. In a dehydrogenation, it can for example be an alkane, such as ethane. In other reactions, such as for example a hydrogenation or a partial oxidation, at least two reactants are required, such as for example hydrogen and an alkine in a hydrogenation, or oxygen and an alkane, such as n-butane in a partial oxidation.

Selectivity is the ability of the adsorbent to select preferentially one of a number of presented compounds in the discharge of the reaction gas.

Adsorbent designates a substance which is capable of concentrating at its boundary surface or absorbing into itself certain substances from gaseous mixtures, which can be linked to an increase in volume. The adsorbent can be a solid or a mixture of solids, such as for example activated carbon, aluminium oxide, silica gel, soot, zeolite, or liquid that is applied onto a solid carrier, such as for example an ethanol solution of N,N-dimethylindoanyline, which is applied to filter paper. These substances can also be used as a mixture. It is possible to provide the adsorbent with reactive groups or to load it with substances, in order thereby to bring about a selective change in property through the contact with the product to be determined.

Properties denote features of the adsorbent which are changed by the contact with the product to be determined. Amongst others, these included optical properties, especially in the infrared, visible or ultraviolet region of the spectrum, i.e. colour changes which can be traced back to the contact of the product with the adsorbent, such as an emergence of colour or a decolourisation, the weight of the adsorbent, the temperature, the fluorescence, the refractive index, the pH value or the conductivity.

The change in property occurring through the contact with the product to be determined must be ascertained according to the invention. Depending on the property, this can take place for example visually or by measurement. It is necessary here to adapt the measurement method to the change in property. A temperature change of the adsorbent that is based on a specific exothermal reaction can for example be determined by means of an infrared camera. The determination can also be automated in the majority of cases.

BRIEF DESCRIPTION OF THE DRAWINGS

An example of embodiment of an arrangement for testing the catalytic activity of solids exposed to a reaction gas will be explained in greater detail below making reference to the drawings.

The drawings show the following.

DETAILED DESCRIPTION

Figure 1:
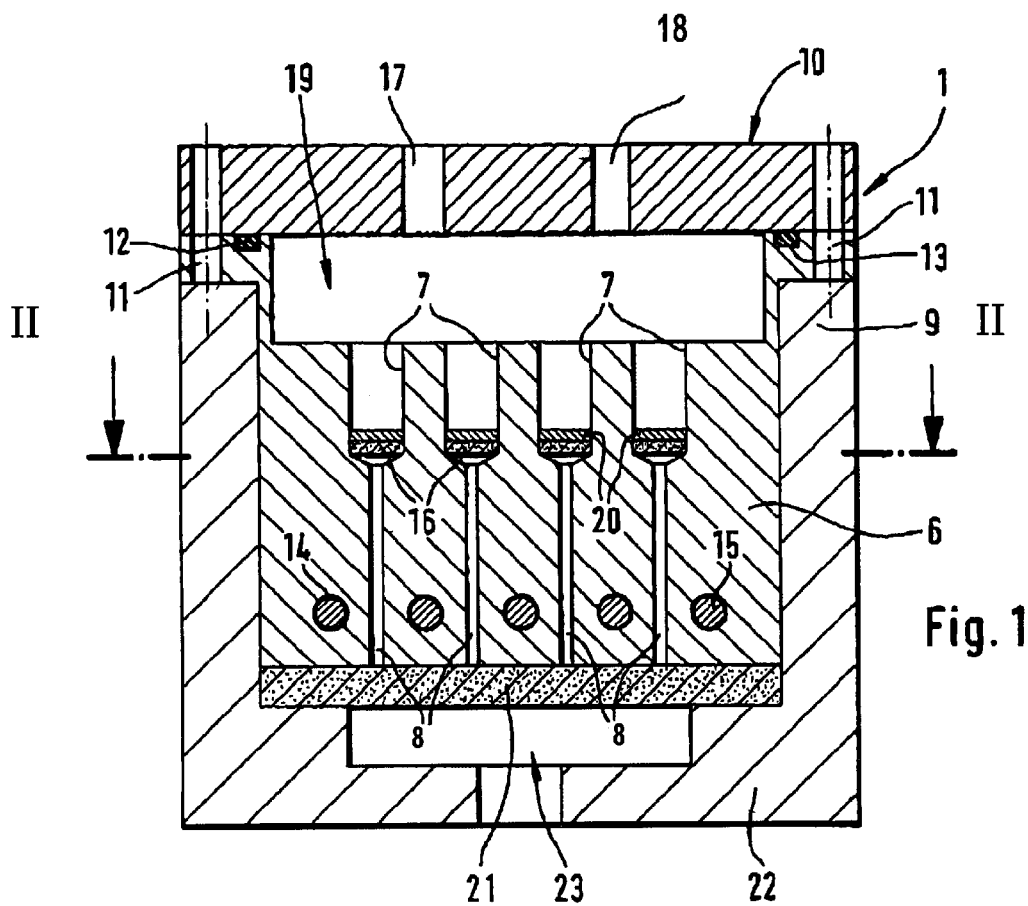
FIG. 1 a cross-sectional representation of the test unit of the arrangement for testing the catalytic activity of solids exposed to a reaction gas, FIG. 2 a section through the test unit along line II—II of FIG. 1.
Figure 2:
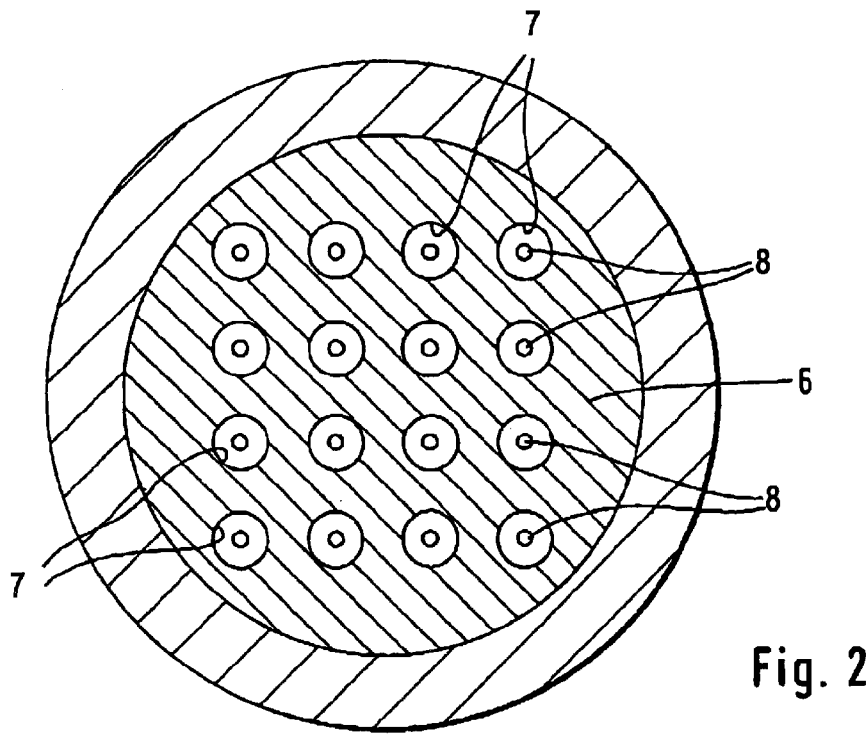

FIG. 1 shows a section through test unit 1 of the test arrangement. Test unit 1 has a cylindrical body 6 made of heat-conducting material, preferably brass, which is provided on its upper side with cylindrical drill-holes 7, which are arranged in the form of an n x m matrix with four lines and four columns (FIG. 2). A 4×4 matrix is given solely by way of example, arrangements with a much larger number of recesses also being possible.

Connected to the bottom of each recess 7 is a channel 8 which ends at the underside of brass body 6 at a porous plate 21. Channels 8 run parallel to one another in a vertical direction. They have a smaller diameter than the recesses. This ensures similar flows through all the recesses, since the channels represent the respective main flow resistances. The individual channels can also be selectively narrowed, in order to adjust exactly the same flows in all the recesses. For this purpose, suitable restrictors or suchlike can be provided in the test unit.

Positioned at the upper side of brass body 6 is a flange 9 for the fixing of a lid 10 made of a heat-conducting material, preferably brass. Flange 9 and lid 10 have a number of drill-holes 11 arranged in a peripheral distribution, so that the lid can be firmly screwed to the brass body (FIG. 3). In order to seal lid 10 against flange 9, an annual seal 12 is provided which sits in an annual groove 13 of flange 9.

Brass body 6 and lid 10 have drill-holes 14 to accommodate heating cartridges 15 of a heating device, in order to allow test unit 1 to be heated up to the reaction temperature. Drill-holes 14 could also serve to accommodate cooling elements, so that a reproducible and controlled temperature management can be ensured.

Positioned at the underside of brass body 6 is a bottom 22 made of heat-conducting material, preferably brass. This bottom 22 can also be screwed to flange 9.

Bottom 22 is used for the fixing of porous plate 21 which can accommodate the adsorbent according to the invention. Bottom 22 has a drill-hole 23 through which the reaction gas, which flows from channels 8 through plate 21, can be conveyed away.

The catalysts to be investigated each sit on a small plate 16 made of a porous inert substance (frit), which is arranged at the bottom of each recess at right angles to its longitudinal axis.

For the simultaneous testing of the catalysts, lid 10 is screwed to flange 9 of brass body 6 and the reaction gas is conveyed via drill-holes 17, 18 provided in the lid into the gas supply chamber 19 located above recess 7. The reaction gas flows through catalysts 20 sitting on frits 16 and is conveyed away via channels 8. At the end of these channels 8 is the adsorbent according to the invention which can for example be applied on a plate 21 made of a porous inert substance (frit) which is placed in the bottom of brass body 6. The reaction gas is then conveyed away via drill-hole 23.

The catalytic conversion of the reaction gas can be carried out for example at temperatures in the range from −50° C. to 600° C. and at pressures in the range from $10^{-3}$ to 1000 bar.

It is possible to automate the process according to the invention. To this end, machines can be used to perform both the loading of the reactors with catalysts, for example by laboratory robots or a loading unit specially provided for the purpose, and the determination of the change in property of the adsorbent, for example by digital photography and then computer-supported evaluation.

The process according to the invention can be used for example to detect products in partial oxidations, such as for example of n-butane or benzene, or in hydrogenation reactions, such as for example of alkines. The use of this method is also advantageous in dehydrogenation reactions, e.g. of alkanes, hydrofomulation reactions of alkenes, amination or acylation reactions. The products of oligomerisation and polymerisation reactions can also be detected with the method described.

In a special application, maleic anhydride is detected from the discharge of a partial oxidation of n-butane in parallel reactors. For this, a filter paper is saturated with an ethanol solution of N,N-dimethylindoanyline and brought into contact with the discharge of the catalytic test. In the presence of maleic anhydride, the colour of the filter paper changes from blue to colourless, which can be traced back to a Diels-Alder reaction of the maleic anhydride with the N,N-dimethylindoanyline with the loss of its conjugated pi-electron system.

What is claimed is:

1. Process for the detection of a product in the discharge of a catalytic material of a plurality of catalytic materials which are exposed to a common supply of a reaction gas, characterized in that the discharge of each catalytic material is fed individually to a common adsorbent, which is selective for a product to be determined, and at least one property of the common adsorbent changes through contact of the common adsorbent with the product to be determined, and at least one changed property of the adsorbent is then ascertained.

2. Process according to claim 1, characterized in that the adsorbent is a solid adsorbent or a liquid adsorbent applied to a solid carrier.

3. Process according to claim 1 or 2, characterized in that the property of the adsorbent changing through the contact with the product to be determined is an optical property.

4. Process according to claim 3, characterized in that the optical property is a color change.

5. Process according to claim 1 or 2, characterised in that the property of the adsorbent changing through the contact with the product to be determined is a fluorescence.

6. Process according to claim 1 or 2, characterised in that the property of the adsorbent changing through the contact with the product to be determined is the weight.

7. Process according to claim 1 or 2, characterized in that the property of the adsorbent changing through the contact with the product to be determined is the temperature.

8. Process according to claim 2, characterised in that the property of the liquid adsorbent changing through the contact with the product to be determined is the refractive index.

9. Process according to claim 2, characterised in that the property of the liquid adsorbent changing through the contact with the product to be determined is the pH value.

10. Process according to claim 1 or 2, characterised in that the property of the adsorbent changing through the contact with the product to be determined is the conductivity.

11. Process according to claim 1 or 2, characterized in that the product to be determined is maleic anhydride and the adsorbent is N,N-dimethylindoanyline, which is applied in ethanol solution onto a filter paper, whereby color of the adsorbent changes from blue to colorless upon contact with the maleic anhydride.

12. Process according to claim 3, characterized in that the product to be determined is maleic anhydride and the adsorbent is N,N-dimethylindoanyline, which is applied in ethanol solution onto a filter paper, whereby color of the adsorbent changes from blue to colorless upon contact with the maleic anhydride.

13. Process according to claim 4, characterized in that the product to be determined is maleic anhydride and the adsorbent is N,N-dimethylindoanyline, which is applied in ethanol solution onto a filter paper, whereby color of the adsorbent changes from blue to colorless upon contact with the maleic anhydride.

14. The process according to claim 3, wherein the optical property comprises an optical property in the infrared, visible or ultraviolet region.

15. The process according to claim 4, wherein the color change comprises emergence of a color or a decolorization.

16. The process according to claim 1, wherein said common adsorbent is spatially separated from said plurality of catalytic materials.

17. The process according to claim 1, further comprising:
   providing support means for said plurality of catalytic materials, and wherein said support means are separate from said common adsorbent.

18. The process according to claim 17, wherein said support means comprises a porous inert substance.

19. The process according to claim 1, further comprising:
   employing a second common adsorbent which is selective to a different product and which has at least one property that changes through contact with the different product, for simultaneous detection of the different product in the discharge of a catalytic material.

20. The process-according to claim 19, wherein said product comprises a desired product of a catalytic reaction, and said different product comprises an undesired by-product of the catalytic reaction, and further comprising:
   determining selectivity of a catalytic material based upon detection of said product and detection of said different product.

* * * * *

UNITED STATES PATENT AND TRADEMARK OFFICE
CERTIFICATE OF CORRECTION

PATENT NO. : 6,537,500 B1
DATED : March 25, 2003
INVENTOR(S) : Brenner et al.

It is certified that error appears in the above-identified patent and that said Letters Patent is hereby corrected as shown below:

Title page,
Item [73], Assignee: "hte Aktiengesellschaft" should be -- hte Aktiengesellschaft the high throughput experimentation company --
Item [30], Foreign Priority Application Data, "September 7, 1998" should be
-- July 9, 1998 --

Signed and Sealed this

Twenty-eighth Day of June, 2005

JON W. DUDAS
*Director of the United States Patent and Trademark Office*